(12) United States Patent
Wozney et al.

(10) Patent No.: US 6,187,742 B1
(45) Date of Patent: *Feb. 13, 2001

(54) METHOD FOR HEALING AND REPAIR OF CONNECTIVE TISSUE ATTACHMENT

(75) Inventors: John M. Wozney, Hudson, MA (US); Scott A. Rodeo, New York; Jo A. Hannafin, New Rochelle, both of NY (US); Russell F. Warren, Greenwich, CT (US)

(73) Assignee: Genetics Institute, Inc., Cambridge, MA (US)

( * ) Notice: Under 35 U.S.C. 154(b), the term of this patent shall be extended for 0 days.

This patent is subject to a terminal disclaimer.

(21) Appl. No.: 09/274,575

(22) Filed: Mar. 23, 1999

Related U.S. Application Data

(63) Continuation of application No. 08/462,497, filed on Jun. 5, 1995, now abandoned, which is a continuation-in-part of application No. 08/362,670, filed on Dec. 22, 1994, now Pat. No. 5,658,882, and a continuation-in-part of application No. 08/798,665, filed on Feb. 11, 1997, now Pat. No. 5,728,679.

(51) Int. Cl.$^7$ ............................................... A61K 37/00
(52) U.S. Cl. ............................. 514/2; 514/12; 530/350; 530/399
(58) Field of Search ...................... 514/2, 12; 530/350, 530/399

(56) References Cited

U.S. PATENT DOCUMENTS

| | | | |
|---|---|---|---|
| 4,877,864 | 10/1989 | Wang et al. | 530/324 |
| 5,013,649 | 5/1991 | Wang et al. | 435/69.1 |
| 5,024,841 | 6/1991 | Chu et al. | 424/422 |
| 5,106,748 | 4/1992 | Wozney et al. | 435/252.3 |
| 5,108,922 | 4/1992 | Wang et al. | 435/240.2 |
| 5,116,738 | 5/1992 | Wang et al. | 435/69.1 |
| 5,141,905 | 8/1992 | Rosen et al. | 435/69.1 |
| 5,171,579 | 12/1992 | Ron et al. | 424/486 |
| 5,187,076 | 2/1993 | Wozney et al. | 435/69.1 |
| 5,206,028 | 4/1993 | Li | 424/484 |
| 5,256,418 | 10/1993 | Kemp et al. | 424/423 |
| 5,658,882 | * 8/1997 | Celeste et al. | |
| 5,728,679 | * 3/1998 | Celeste et al. | |

FOREIGN PATENT DOCUMENTS

| | | |
|---|---|---|
| WO 91/18098 | 11/1991 | (WO) . |
| WO 93/00432 | 1/1993 | (WO) . |
| WO 95/00050 | 1/1993 | (WO) . |
| WO 93/09229 | 5/1993 | (WO) . |
| WO 93/16099 | 8/1993 | (WO) . |
| WO 94/15949 | 7/1994 | (WO) . |
| WO 94/15966 | 7/1994 | (WO) . |
| WO 94/21681 | 9/1994 | (WO) . |
| WO 94/26892 | 11/1994 | (WO) . |
| WO 94/26893 | 11/1994 | (WO) . |
| WO 95/01801 | 1/1995 | (WO) . |
| WO 95/01802 | 1/1995 | (WO) . |

OTHER PUBLICATIONS

Rodeo Sa et al., "Bone Morphogenetic Protein Enhances Early Tendon Healing in a Bone Tunnel," *Orthopaedic Research Society*, 41 Annual Meeting, Orlando, Florida, Feb. 13–16, 1995, p. 288.

* cited by examiner

Primary Examiner—Ardin H. Marschel

(57) ABSTRACT

Methods and compositions are provided for the treatment of defects and disease involving the functional attachment of connective tissue, such as tendon or ligament, to bone. Preferred methods comprise administering a composition containing a bone morphogenetic protein and a suitable carrier. The method results in the regeneration of functional attachment between the connective tissue and bone, such that minimal fibrous or granulation tissue is formed at the interface between the regenerated bone and connective tissue. The method and composition are useful for augmenting tissue grafts in reconstructive surgery. The method and compositions result in closer apposition of bone to the connective tissue at earlier time points and increased strength of fixation at earlier time points.

14 Claims, No Drawings

METHOD FOR HEALING AND REPAIR OF CONNECTIVE TISSUE ATTACHMENT

This application is a continuation of U.S. Ser. No. 08/462,497, filed Jun. 5, 1995, now abandoned, which is a continuation-in-part of U.S. Ser. No. 08/362,670, filed Dec. 22, 1994, now U.S. Pat. No. 5,658,882, and U.S. Ser. No. 08/798,665, filed Feb. 11, 1997, now U.S. Pat. No. 5,728,679.

FIELD OF THE INVENTION

The present invention relates to the field of tissue repair, specifically, the regeneration of a functional attachment between connective tissue, such as tendon, cartilage or ligament, to bone. This functional attachment may be destroyed by trauma or stress, or by degenerative or congenital disease. Thus, the present invention may be useful in reconstructive surgery or other procedures for the regeneration of a functional attachment between connective tissue and bone.

BACKGROUND OF THE INVENTION

Background of the incidence and etiology of need:

Although several of reconstructive surgical procedures rely on the firm healing or attachment of connective tissue, particularly tendon or ligament, to bone, little is known about the healing process at the tendon-to-bone interface. Since the site of graft fixation to bone represents the weakest area in the early post-transplant period, methods to improve early graft fixation strength have significant clinical application. This is of particular importance in operations on the knee, shoulder, hip, hand, ankle and elbow.

The development of tendon or ligament insertion into bone is poorly understood. The insertion site is mediated by collagen fibers, known as "Sharpey's fibers," which are continuous from tendon into bone. Sharpey's fibers are thought to form in the developing skeleton by progressive mineralization of ligament or periosteal collagen fibers by advancing bone during growth. Studies have indicated that bone heals to tendon by bone ingrowth into the fibrovascular interface tissue which initially forms between the tendon and bone. There is progressive mineralization of the interface tissue with subsequent bone ingrowth into the outer tendon. Despite the evidence that bone grows into collagenous tissue, the mechanism of such bone ingrowth, and the effectiveness and strength of the attachment, remains uncertain. A previous study of tendon-to-bone healing demonstrated the formation of a fibrous tissue interface between the tendon and bone. Rodeo et al., *J. Bone and Joint Surgery*, 75-A: 1795–1803 (1993).

Accordingly, despite substantial endeavors in this field, there remains a need for an effective method of repair of a functional attachment between connective tissue, such as tendon or ligament, and bone.

SUMMARY OF THE INVENTION

The present invention provides methods and compositions for regenerating a functional attachment between connective tissue and bone. In particular, the present invention comprises methods of treating patients with detached or degenerated attachments of the tendon or ligament to bone. Some examples include reconstructive surgery on the knee, shoulder, hand, ankle and elbow. Particular areas where the present invention may prove useful include reconstruction of the anterior cruciate ligament (ACL), or the rotator cuff. The methods and compositions of the present invention are advantageous in that they utilize osteogenic proteins, which may be produced via recombinant DNA technology, and therefore are of potentially unlimited supply. The methods and compositions of the present invention are further advantageous in that regeneration of the attachment apparatus may be accelerated or may be of greater ultimate strength, and the attachment formed between connective tissue and bone may reach a functional strength sooner after surgery or repair is effected. The methods and compositions of the present invention are further advantageous in that they induce the regeneration of the functional attachment between connective tissue and bone, while minimizing or avoiding formation of fibrous or granulation tissue at the interface between tissue types.

The methods of the present invention are particularly applicable to the fixation of a round tendon in a bone tunnel or a flat tendon onto a bone surface. Several clinical examples are relevant. A common clinical example is reconstruction of the anterior cruciate ligament (ACL). Reconstruction may be performed by using the central third of the patellar tendon with an attached bone block from both the tibia and patella, or by using the semitendinosus and gracilis tendons. Benefits of the use of patellar tendon include immediate bony fixation allowing aggressive post-operative rehabilitation and increased strength. However, the use of central third patellar tendon has been associated with adverse sequelae, including patellar fracture, patellar ligament rupture, and degeneration of the patellofemoral joint. Benefits of the use of semitendinosus and gracilis tendons include easier graft harvest, no disruption of the extensor mechanism of the knee, greater quadriceps strength one year post-operatively, and minimal loss of hamstring strength. The major pitfall is concern about the strength of fixation of the tendon within bone tunnels and risk of graft failure at the fixation site. The major difference between these two methods of ligament reconstruction is fixation of the graft.

The use of BMP to augment tendon-to-bone healing may result in better methods to utilize semitendinosus and gracilis tendons for ACL reconstruction, thus obviating the patellar defect and concomitant extensor mechanism disruption inherent in patellar ligament harvest. Preclinical evaluations indicate that rhBMP-2 improves early healing of bone to a tendon graft, as demonstrated by histologic and biomechanical evaluation. Increased strength of tendon-to-bone fixation will allow earlier and more aggressive rehabilitation, resulting in earlier return to normal activities, work, or sport.

Other common clinical examples for which the invention has direct application include the following: rotator cuff tendon repair to the greater tuberosity of the humerus, reattachment of the glenoid labrum to the scapular neck, reconstruction of the lateral ankle ligaments using a tendon graft placed through bone tunnels, reconstruction of the medial collateral ligament of the elbow or knee using a tendon graft fixed to the surface of the bone or through bone tunnels, reconstruction of the ulnar collateral ligament of the thumb using a tendon graft placed in a bone tunnel, and repair of the flexor or extensor tendons of the digits into bone tunnels or to the surface of the bone of the phalanges. The invention is broadly applicable to any situation in which connective tissue (tendon, ligament, labrum, fascia, or joint capsule) is reattached to bone, either to the surface of the bone or into a tunnel in the bone.

DETAILED DESCRIPTION OF THE INVENTION

According to the present invention, methods and compositions are provided for treatment of patients who require reconstructive surgery for repair of the functional attachment between connective tissue and bone. The methods and composition are advantageous in that repair or improvement of the entire attachment apparatus may be effected: the tendon or ligament, the adjacent bone, as well as the functional attachment. The methods comprise applying to the site in need of reconstructive surgery, or to the site of a defect, tear or detachment of connective tissue to bone, an amount of a composition comprising one or more purified osteogenic proteins which is effective to regenerate the functional attachment of the connective tissue to the bone. The method may further comprise the administration of a composition comprising a purified or recombinant osteogenic protein to a site in need of regeneration of the connective tissue to bone attachment in a suitable carrier such that the connective tissue, the bone, and the functional attachment apparatus are regenerated, with reduced fibrous or granulation tissue at the site of attachment occurring. The composition is preferably administered in combination with an effective carrier. One of the key advantages of the method of the present invention is that it allows for the controlled regeneration of connective tissue, bone and the functional attachment apparatus in an accelerated manner such that the attachment may attain greater functional strength, at an earlier time point than with a similar procedure performed without the addition of osteogenic proteins.

OSTEOGENIC PROTEIN

The osteogenic protein is preferably from the subclass of proteins known generally as bone morphogenetic proteins (BMPs), which have been disclosed to have osteogenic activity, and other growth and differentiation type activities. These BMPs include BMP-2, BMP-4, BMP-5, BMP-6, BMP-7, BMP-8, BMP-9, BMP-10, BMP-11, BMP-12, and BMP-13, and may also include other members of the TGF-β superfamily of proteins, such as growth and differentiation factors, or GDFs, and MP52. The structures of a number of BMP proteins are disclosed in U.S. Pat. Nos. 4,877,864; 5,108,922; 5,013,649; 5,116,738; 5,106,748; 5,187,076; 5,141,905; and in PCT applications WO 91/18098; WO 93/00432; WO 94/26893; and WO 94/26892; and in co-pending patent application, Ser. No. 08/362,670, filed on Dec. 22, 1994. The structure of a number of GDFs are disclosed in WO 94/15965, WO94/15949; WO95/01801; WO95/01802; WO94/21681; WO94/15966. The structure of MP52 is disclosed in WO93/16099. The disclosures of the above applications are hereby incorporated by reference. The BMP is preferably BMP-2, the sequence of which is disclosed in U.S. Pat. No. 5,013,649, the disclosure of which is hereby incorporated by reference. Other BMPs known in the art can also be used. Presently, the most preferred BMP is BMP-2.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the specification of which is hereby incorporated herein by reference. The amount of osteogenic protein useful herein is that amount effective to stimulate increased osteogenic activity of infiltrating progenitor cells, and will depend upon the size and nature of the defect being treated, as well as the carrier being employed. Generally, the amount of protein to be delivered is in a range of from about 0.05 to about 1.5 mg.

In a preferred embodiment, the osteogenic protein is administered together with an effective amount of a protein which is able to induce the formation of tendon- or ligament-like tissue. Such proteins, include BMP-12, BMP-13, and other members of the BMP-12 subfamily, as well as MP52. These proteins and their use for regeneration of tendon and ligament-like tissue are disclosed in United States application serial number Ser. No. 08/362,670, filed on Dec. 22, 1994, presently issued as U.S. Pat. No. 5,658,882, the disclosure of which is hereby incorporated herein by reference. In another preferred embodiment, a heterodimer in which one monomer unit is an osteogenic protein such as BMP-2, and the other monomer subunit is a tendon-inducing protein, such as BMP-12, is administered in accordance with the methods described below, in order to induce the formation of a functional attachment between connective tissue and bone.

CARRIER

Materials which may be useful as the carrier in practicing the present invention include pharmaceutically acceptable materials having viscosity and polarity such that, when added to the bone morphogenetic protein, form a composition that possesses appropriate handling characteristics (i.e., is neither too runny to remain at the defect site) for application to the site of reconstruction of the connective tissue to bone attachment. Adding the carrier to the bone morphogenetic protein allows the protein to remain in the disease or lesion site for a time sufficient to allow the protein to increase the otherwise natural rate of regenerative osteogenic activity of the infiltrating mammalian progenitor cells, and to form a space in which new tissue can grow and allow for ingrowth of cells. The carrier may also allow the bone morphogenetic protein to be released from the defect or lesion site over a time interval appropriate for optimally increasing the rate of regenerative osteogenic activity of the progenitor cells.

The most preferred family of carriers comprises collagenous materials. Preferred collagen materials include Collastat® and Helistat® collagen sponges (Integra LifeSciences Corp., Plainsboro, N.J.). Other collagen materials which may be suitable for use in the present invention are described in U.S. Pat. No. 5,206,028; U.S. Pat. No. 5,024,841; U.S. Pat. No. 5,256,418. The collagen carrier is preferably in the form of a sponge. The collagen sponge may be loaded with protein prior to administration by soaking the sponge in the desired volume and concentration of protein for a suitable time period. The collagen sponge is preferably soak loaded with protein in a range from about 10% to about 150% v/v [ml protein/cc dry sponge], more preferably about 10 to about 60% v/v. Alternatively, the protein may be adsorbed to the collagen sponge during production. In this case, bone morphogenetic protein is preferably added to the collagen sponge during production and lyophilized to form a unitary product. The protein is preferably added in a ratio of from about 10 to about 150% v/v, more preferably in a range from about 60 to about 80% v/v. Other forms of collagen which may be useful in the present invention are collagen gel, and cross-linked polymeric collagen.

Another preferred family of carriers for administration of the bone morphogenetic proteins are porous particulate polymers, described in detail in U.S. Pat. No. 5,171,579, the entire disclosure of which is incorporated herein by reference. Preferably the porous particulate polymers are co-polymers of polylactic and polyglycolic acid. The protein and polymers are preferably sequestered by a sequestering agent, such as autologous blood. An alternative carrier useful for the present invention is a formulation of osteogenic protein, porous particulate polymers and another sequestering agent, such as cellulosic material. Other preferred sequestering agents include hyaluronic acid, sodium alginate, poly(ethylene glycol), polyoxyethylene oxide, carboxyvinyl polymer and poly(vinyl alcohol). Most preferred as the sequestering agent for this embodiment is carboxymethylcellulose. These compositions are described in published PCT application WO 93/00050, the entire disclosure of which is hereby incorporated herein by reference. The cellulosic protein sequestering agent is preferably present in a concentration of about 1 to about 10% (w/v implant). The porous particulate polymer/cellulosic sequestering agent may optionally be further combined with aqueous glycerol as a diluent, preferably in concentrations of about 10 to about 80% (v/v); and ratios of sequestering agent/liquid solution:porous particulate polymers are preferably from about 0.1 to about 0.9 (v/v). Alternatively, the porous particulate polymers may be formed into a fused sponge, as described in co-pending application Ser. No. 08/308,787, filed on Sep. 19, 1994, the disclosure of which is hereby incorporated by reference. The amount of osteogenic protein used with porous particulate polymers is generally in the range of 0.01 to 1 mg of protein, preferably 0.05 to 0.6 mg protein for each cubic centimeter of composition employed.

Another preferred family of carriers is cellulosic materials such as alkylcellulose (including hydroxyalkylcellulose), including methylcellulose, ethylcellulose, hydroxyethylcellulose, hydroxypropylcellulose, hydroxypropylmethylcellulose, and carboxymethylcellulose, the most preferred being the cationic salts of carboxymethylcellulose (CMC).

In the case of cellulosic carriers and collagen gels, it is preferred that the carrier be in the form of a hydrated cellulosic viscous gel. Viscosity may be increased through mechanical means, such as high agitation for a suitable period of time, followed by autoclaving, or chemically. The BMP and cellulosic carrier is preferably in a solution of suitable buffer. One preferred buffer solution is a composition comprising, in addition to the osteogenic protein, about 1.0 to about 10.0% (w/v) glycine, about 0.1 to about 5.0% (w/v) of a sugar, preferably sucrose, about 1 to about 20 mM glutamic acid hydrochloride, and optionally about 0.01 to about 0.1% of a non-ionic surfactant, such as polysorbate 80. Preferred solutions are from about 1% to about 20% w/v cellulosic carrier/buffer. If desired, a salt may be added. A preferred viscous gel carrier is described in Example 2 below. The amount of osteogenic protein useful with viscous gel carrier is generally in a range of from about 0.05 to about 1.5 mg, preferably from about 0.1 to about 1.0 mg per cubic centimeter of implant material required.

Other materials which may be suitable for use as carriers for BMPs in the methods and compositions of the present invention include hyaluronic acid, surgical mesh or sutures, polyglyconate, temperature-sensitive polymers, demineralized bone, minerals and ceramics, such as calcium phosphates, hydroxyapatite, etc., as well as combinations of the above described materials.

In one preferred embodiment of the present invention, however, no carrier is employed. Instead, the protein of the present invention, in a suitable buffer such as that described above, is applied directly to the site in need of tissue repair. For example, the protein may be applied using a brush or other suitable applicator, such as a syringe for injection. Alternatively, the protein may be directly applied to the site in need of tissue repair.

The following examples further describe the practice of embodiments of the invention with BMP-2 in a collagen sponge carrier. The examples are not limiting, and as will be appreciated by those skilled in the art, can be varied in accordance with the above specification.

EXAMPLES

Example 1

BMP-2 and Collagen Sponge Polymer Carrier in Surgically Created Tendon to Bone Detachment Defects Twenty adult mongrel dogs were used. The long digital extensor tendons of both knee joints were detached from their femoral insertion and transplanted through a drill hole in the proximal tibial metaphysis. The long digital extensor tendon of the knee joint of both hind limbs was detached from its femoral insertion and was transplanted, through a bone tunnel, into the proximal tibial metaphysis. Recombinant human BMP-2 (rhBMP-2) was applied to the tendon-bone interface in one limb, using a Type I collagen sponge as a carrier [FIG. 1]. The contralateral limb received the collagen sponge with no rhBMP-2 [control].

The animals were anesthetized during surgery. The knee joint was approached through a lateral parapatellar incision; the long digital extensor tendon was identified and then was detached from its insertion on the lateral femoral condyle by sharp dissection. The fascia over the anterior tibialis muscle then was incised, and the muscle was retracted laterally. A drill-hole, 4.8 mm in diameter, was made in the proximal tibial metaphysis at a 45-degree angle to the long axis of the bone. Helista® collagen sponge was loaded with recombinant human BMP-2 (rhBMP-2), and the sponge was then wrapped around the detached tendon. The free end of the tendon was pulled manually through the drill-hole and was fixed, under tension, on the medial aspect of the proximal tibial metaphysis with simple interrupted sutures of 4-0 stainless steel. The tendon fit snugly into the bone tunnel and was in contact with bone throughout the length of the tunnel. The joint capsule, fascia, and subcutaneous tissues were closed with interrupted sutures of 3-0 chromic gut, and the skin was closed with interrupted sutures of 3-0 stainless steel. The procedure then was done on the contralateral knee. The limbs were not immobilized and the dogs were allowed exercise ad libitum in individual indoor runs.

Eight dogs were sacrificed at two and four weeks; four dogs were sacrificed at eight weeks. High resolution radiographs were made and microscopic sections of the tendon-bone interface were examined under light and polarized light microscopy. Tetracycline-labelled sections were examined under fluorescent microscopy. Biomechanical testing of ultimate load to failure was performed for the two and four week specimens on an MTS materials test machine at a strain rate of 50.8 mm/second. The failure loads were averaged and the rhBMP-2 treated side was compared to the control side using a Student's paired t-test.

Results: Serial histologic analysis revealed extensive proliferation of fibroblasts, plump osteoblast-like cells, and new bone trabeculae in the tendon-bone interface in the rhBMP-2 treated limbs, compared with limbs that received the collagen carrier only. As healing progressed, the new bone trabeculae in the interface in the rhBMP-2 treated limbs matured and were in closer proximity to the tendon, while in the limb without rhBMP-2, there was a zone of fibrous or granulation tissue separating the tendon and the bone tunnel. Von Kossa stained sections and fluorescent microscopy of fluorochrome-labelled specimens demonstrated progressive mineralization of the newly formed bone in the tendon-bone interface. High resolution radiographs demonstrated that during the bone induction process, the pre-existing lamellar bone was resorbed and new bone was observed to progressively mineralize in the four and eight-week rhBMP-2 specimens. There was no evidence of host immunologic response to the collagen implant.

Paired comparisons of ultimate failure strength (N) demonstrated that the rhBMP-2 treated limbs were significantly stronger in both the two week specimens (p=0.035) and the four week specimens (p=0.05). There was a statistically significant increase in strength from two to four weeks in the rhBMP-2 treated limbs (p=0.02) and the control limbs (p=0.005). [FIG. 2].

Discussion: Bone morphogenetic protein enhances the healing of a tendon graft in a bone tunnel. A previous study of tendon-to-bone healing demonstrated a fibrous tissue interface between the tendon and bone. In the present study, rhBMP-2 induced extensive new bone deposition in this interface tissue, resulting in closer apposition of bone to the tendon at earlier time points and more regular establishment of Sharpey's fibers between the tendon and the bone in the rhBMP-2-treated limbs. The increased strength of fixation correlates with the histologic degree of bone ingrowth seen in the rhBMP-2 treated limbs.

We claim:

1. A method for regeneration of a functional attachment between ligament and bone comprising administering to an area in need of regeneration of said functional attachment a pharmaceutically acceptable composition containing purified bone morphogenetic protein (BMP) in an amount sufficient to cause regeneration of the functional attachment of ligament to bone.

2. A method according to claim 1, wherein the composition comprises recombinant human BMP-2 in a suitable carrier.

3. A method according to claim 2, wherein the carrier comprises a collagen sponge.

4. A method according to claim 2, wherein the carrier is selected from the group consisting of:
   a) collagen sponge;
   b) cellulosic viscous gel; and
   c) porous particulate polymers and a sequestering agent.

5. A method according to claim 1, wherein the composition comprises recombinant human BMP-12 in a suitable carrier.

6. A method according to claim 5, wherein the composition comprises BMP-2 and BMP-12 in a suitable carrier.

7. A method for regeneration of a functional attachment between ligament and bone comprising administering to an area in need of regeneration of said functional attachment a pharmaceutically acceptable composition containing one or more BMPs selected from the group consisting of:
   a) BMP-2;
   b) BMP-12; and
   c) heterodimers of BMP-2 and BMP-12.

8. A method for regeneration of a functional attachment between tendon and bone, said method comprising applying to a site in need of regeneration of such attachment, a pharmaceutically acceptable composition containing an effective amount of a bone morphogenetic protein.

9. A method according to claim 8, wherein the composition comprises recombinant human BMP-2 in a suitable carrier.

10. A method according to claim 9, wherein the carrier comprises collagen sponge.

11. A method according to claim 9, wherein the carrier is selected from the group consisting of:
    a) collagen sponge;
    b) cellulosic viscous gel; and
    c) porous particulate polymers and a sequestering agent.

12. A method according to claim 8, wherein the composition comprises BMP-12 in a suitable carrier.

13. A method according to claim 12, wherein the composition comprises BMP-2 and BMP-12 in a suitable carrier.

14. A method for regeneration of a functional attachment between tendon and bone, said method comprising applying to a site in need of regeneration of such attachment, a pharmaceutically acceptable composition containing one or more BMPs selected from the group consisting of:
    a) BMP-2;
    b) BMP-12; and
    c) heterodimers of BMP-2 and BMP-12.

* * * * *